United States Patent [19]

Kleinschmitt et al.

[11] Patent Number: 5,466,946

[45] Date of Patent: Nov. 14, 1995

[54] METHOD AND APPARATUS FOR DISCRIMINATING BETWEEN LIQUIDS AND GASES

[75] Inventors: David Kleinschmitt; Maroun Touma; George E. Zabetakis, all of Bethel, Conn.

[73] Assignee: Miles, Inc., Tarrytown, N.Y.

[21] Appl. No.: 349,143

[22] Filed: Dec. 2, 1994

Related U.S. Application Data

[63] Continuation of Ser. No. 106,255, Aug. 13, 1993, abandoned.

[51] Int. Cl.$^6$ ..................................................... G01N 15/06
[52] U.S. Cl. ............................................. 250/577; 73/291
[58] Field of Search ................................... 250/577, 576, 250/902, 906; 356/436, 437; 73/293, 327, 291; 128/766, DIG. 22

[56] References Cited

U.S. PATENT DOCUMENTS

| | | | |
|---|---|---|---|
| 4,253,846 | 3/1981 | Smythe et al. | |
| 4,344,429 | 8/1982 | Gupton et al. | 250/577 |
| 4,366,384 | 12/1982 | Jensen | 250/577 |
| 4,665,391 | 5/1987 | Spam | 250/577 |
| 4,859,864 | 8/1989 | Smith | 250/577 |

FOREIGN PATENT DOCUMENTS

| | | |
|---|---|---|
| 2660755 | 10/1991 | France. |
| 2664698 | 1/1992 | France. |

OTHER PUBLICATIONS

Journal of Physics E. Scientific Instruments, vol. 22, No. 10, Oct. 1989, pp. 827–833.

*Primary Examiner*—Edward P. Westin
*Assistant Examiner*—Que T. Le
*Attorney, Agent, or Firm*—Sprung Horn Kramer & Woods

[57] ABSTRACT

An apparatus and method for detecting a liquid/gas interface flowing in a transparent tube comprises directing light radially through the transparent tube orthogonal to its longitudinal axis such that the radially directed light passing through the tube when filled with liquid thereat will extend substantially within a predetermined zone and when filled with gas thereat will extend beyond the predetermined zone. Light is received at a position diametrically opposite to a position from which light is directed by receiving only light passing through the tube and extending beyond the predetermined zone. An output signal representative of liquid or gas in the tube is produced in response to the amount of light received. A second light receiver disposed outside the zone is used to determine the direction of flow.

13 Claims, 2 Drawing Sheets

| STATUS SIGNALS | | |
|---|---|---|
| INITIAL | MOTION RIGHT | MOTION LEFT |
| 11 | 01 | 10 |
| 10 | 11 | 00 |
| 00 | 10 | 01 |
| 01 | 00 | 11 |

5,466,946

METHOD AND APPARATUS FOR DISCRIMINATING BETWEEN LIQUIDS AND GASES

This application is a continuation of application Ser. No. 08/106,255, filed Aug. 13, 1993, now abandoned.

BACKGROUND OF THE INVENTION

The present invention is directed to a method and apparatus for the discrimination between liquid and air in a segmented flowing stream, such as one found in analytical instrumentation, e.g., a clinical chemistry analyzer.

Devices of this type, called bubble detectors in these systems, are known in the prior art and use dedicated light sources, such as light emitting diodes with relay optics such as lenses and apertures close to the liquid carrying tube to transmit light through the tube to a photodetector on the opposite side of the stream. Discrimination between liquid and air results from changes in the light concentration on the photodetector due to the difference in the refractive index of air and liquid within the tube. Because the light passes through the liquid on the way to the detector, variations in absorbance characteristics of the liquid can influence the intensity of light striking the photodetector, thereby affecting the ratio of air to liquid signal.

In other prior art optical bubble detectors, a separate light path is used adjacent to a colorimetric optical path, resulting in a bubble detection signal offset in time from the analytic signal. Because of this offset, timing compensation is required when taking data on segments of the stream entering the colorimetric optical path. This is especially problematic when the stream does not have a constant velocity and the time can vary from the bubble detector position to the colorimetric position of the tube.

Moreover, the signal level of these known detection systems rely on the focusing effect of the liquid within the tube to increase the signal level, while air in the tube reduces the signal level enabling discrimination between the two. The wavelength of the bubble detector light must be chosen to avoid absorption of the bubble detector light by the liquid within the tube and provisions must be made to prevent the bubble detector light from influencing the colorimetric measurement.

SUMMARY OF THE INVENTION

The main object of the present invention is to provide an improved optical method and apparatus for discriminating between liquid and air in a segmented flowing stream.

Another object is to provide an improved method and apparatus for analytical instrumentation of the type which uses fiber optics to illuminate a transparent tube containing the segments and to collect the transmitted light.

Still another object of the present invention is to produce a detection signal which has high liquid to air ratios and is not affected by variations in light absorption by the liquid.

A further object of the present invention is to provide a method and apparatus which shares portions of the existing fiber optics used for analytical detection of a component in a liquid segment, e.g., by colorimetry to enable compact packaging of the optical portion of the bubble detector.

A still further object of the present invention is to provide a method and apparatus capable of additionally detecting the direction of flow of the segments.

The present invention has the advantage of eliminating the need for a separate light source dedicated to bubble detection and provides freedom from liquid absorption influencing detection signal levels. Another advantage of the present invention is that no additional optical elements are required near the tube beyond those already necessary for the analytic detection. Still further, the method and apparatus according to the present invention eliminates the bubble detecting signal time offset from the analyzer signal.

The present invention enables the acquisition of bubble detection information at the same time as analytical information by tapping off a portion of the light from the light source after it passes through the tube, so that no timing compensation is required regardless of variations in stream velocity. Moreover, the bubble detection signal is virtually unaffected by light absorption by the liquid, since the maximum bubble detector signal is obtained when there is air in the tube rather than liquid. Liquid of any absorbance results in a lower signal, and thus liquid of high absorbance will merely result in a far lower signal. Because the light source is used for bubble detection as well, there is no interference between bubble detection and the analytical signal.

The bubble detection function is preferably carried by a detector or light receiving means, such as a small fiber bundle located away from the axis of the light source and above the analytical detection means. The angle that the fiber bundle is disposed at is dependent on the dimensions of the tube and the size of the illuminating fiber optics. In one embodiment the angle is from 23 to 45 degrees, preferably 30 to 38 degrees. The maximum signal occurs when air in the tube decreases the overall refractive bending of the light, allowing a portion of it to reach the bubble detection means. The lowest signal occurs when liquid in the tube increases the overall refractive bending of the light along the axis of entry and draws the light away from the bubble detector means. Since the signal level is low when liquid is in the tube, adding dyes or particles that absorb light actually enhances the ability to discriminate liquid from air.

The problem of detecting the direction of flow is solved by adding a second bubble detection means, e.g., a second fiber bundle, in close proximity to the first bubble detection means. The spacing of the two bubble detection means must be less than the length of the smallest segment of the stream. A unique set of logic state transitions that occur at the bubble detectors when the stream moves to the left or right starting from any of four possible initial conditions enables the system to detect flow direction. By sampling the bubble detector outputs at a rate faster than the stream can move past the two bubble detectors, one can accurately determine changes in the status of the detectors. Interpretation of the status by logic circuitry allows the determination of the direction of the stream and allows one to count the segments flowing past the analytical detection means.

These and other objects and advantages and features of the present invention will be apparent from the following detailed description of the invention with reference to the attached drawings, wherein

DETAILED DESCRIPTION OF THE INVENTION

Figure 1:
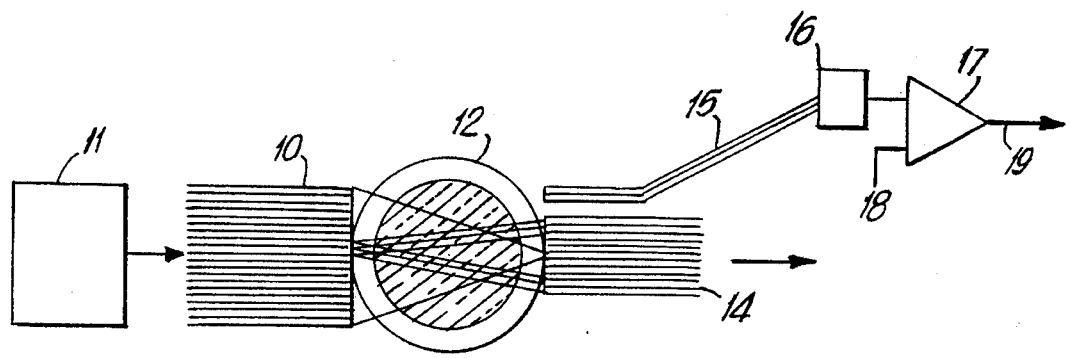
FIG. 1 is a schematic cross-section of the present invention showing a tube with liquid therein.
Figure 2:
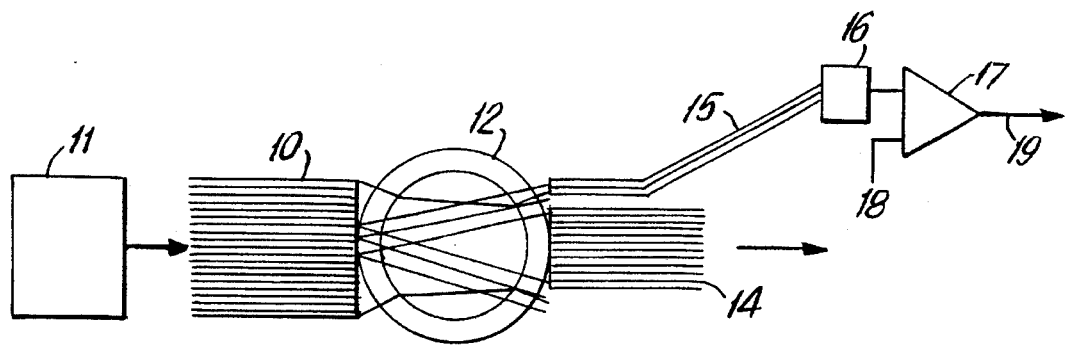
FIG. 2 shows the schematic cross-section of FIG. 1 with gas in the tube.

FIGS. 1 and 2 are schematic cross-section drawings of the air liquid interface discrimination method and apparatus according to the present invention. It is noted that the present invention can be applied to a variety of apparatuses which create the flow of liquid and gas segments in an elongated tube. Such an apparatus that is of particular interest and in which liquid and gas segments flow with reversing directions is shown in detail in copending U.S. application Ser. No. 07/846,269 filed Feb. 26, 1992, the disclosure of which is incorporated herein by reference.

An apparatus according to the present invention comprises an illumination fiber optic bundle 10 which receives input light from light source 11 which is conventionally used for colorimetric analysis, i.e., a tungsten-halogen lamp producing white light, and directs the light through the diameter of the transparent tube 12 and orthogonal to the longitudinal axis of the tube through which an air and liquid segmented flowing stream passes and which travels along the longitudinal axis.

Figure 3A:
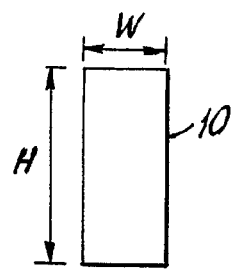
FIG. 3a is a front view of the illumination fiber optic bundle of FIG. 1.
Figure 3B:
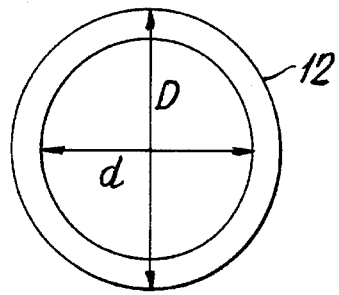
FIG. 3b is a cross-section of the tube of FIG. 1.
Figure 3C:
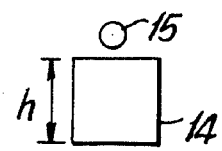
FIG. 3c is a front view of the receiving fiber optic bundle of FIG. 1.

Diametrically opposed on the other side of the tube 12, is a collection fiber optic bundle 14 which directs light to a colorimeter analyzer (not shown) in a conventional manner and a smaller fiber optic bundle 15 which constitutes bubble detector fibers and only receives light outside a predetermined zone in which bundle 14 is disposed. The limits of the predetermined zone are preferably defined by the area of the bundle 14 as shown in FIG. 3c. The light output of bundle 15 is input to a photodiode 16 which converts the light to electrical energy which is received by a comparator 17 and which compares the output of the photodiode 16 to a reference voltage 18 and generates a control signal 19.

As shown in FIG. 1, when the tube contains liquid, the light from the illuminating fiber optic is bent or refracted when passing through the liquid filled tube so that substantially none of the light rays extend outside the zone and reach the collecting fiber bundle 15 which is solely intended for bubble detection. The resultant bubble detector signal from the photodiode 16 is low, i.e., below the reference voltage, so that the comparator 17 produces a control signal having a first level which indicates that there is liquid in the tube.

As shown in FIG. 2, the light rays in the air filled tube are not bent or refracted as severely, and consequently, a significant portion of the light is disposed beyond the zone and is collected by the bubble detector fibers 15 resulting in a bubble detector signal from the output of photodiode 16 which is high. When the bubble detector signal rises above the reference voltage 18, the comparator 17 produces the control signal with a second level which indicates that a gas is in the tube.

In operation, light source 11 is on all the time and the stream through tube 12 is monitored by sampling the signal of 19 at a rate which is at least twice the velocity of the stream. The resulting control signals will produce an accurate representation of the segments flowing in the tube.

Whereas the embodiment in FIGS. 1 and 2 shows the bubble detector fibers 15 on top of the collection fiber bundle 14, those skilled in the art will readily recognize that the bubble detector fibers can also be below the collection fiber optic bundle or both above and below the collection fiber optic bundle 14 as long as it is outside the predetermined zone.

The height of illuminating and collecting fiber optics and their proximity to the tube must be chosen to assure sufficient light bending or refraction so that substantially none of the rays impinge upon the bubble detector fibers when liquid is in the tube. The considerations for the geometry of the fibers with respect to the tube is shown in connection with FIGS. 3a–c.

As shown therein, in one embodiment the tube 12 has an inner diameter d of 2.2 mm and an outer diameter D of 2.5 mm. The height of the illumination fiber optic bundle H is 2 mm and the width W is 1 mm. The collection fiber bundle is a square with a side h of 1 mm. The bubble detector fibers 15 have a diameter of 0.36 mm, with its center disposed 0.85 mm from the center of bundle 14. Fibers 15 are disposed 34 degrees off the axis of the illumination fiber optic bundle 10.

As a result of the above, the bubble detector has freedom from liquid absorption influence on the output signal. When liquid is in the tube, the signal level is already low because of lack of light and is only enhanced by being further deprived of light by the absorption of the liquid.

Figure 4:
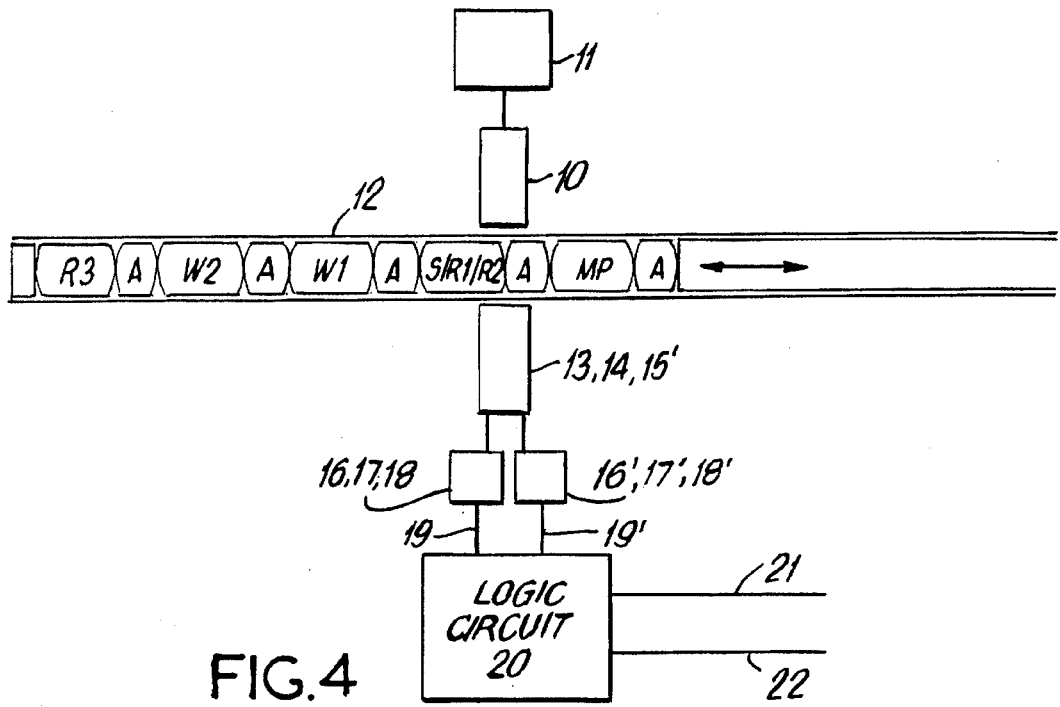
FIG. 4 is a block diagram of an embodiment of the invention wherein direction is also detected.

FIG. 4 shows another embodiment of the present invention wherein the direction of flow is detected in addition to the detection of a liquid/gas interface. The apparatus disclosed in the aforementioned pending U.S. application, which has been incorporated herein by reference, discloses the operation of a tube wherein flow is reversible. Thus, it is important to know in addition to the fact that a liquid/gas interface is present, in which direction that interface is traveling.

Figure 5:
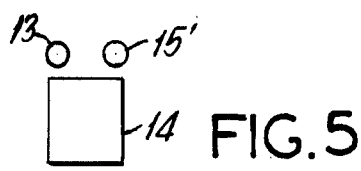
FIG. 5 is a front view of the receiving fiber optic bundle of FIG. 4.

Thus, in accordance with the present invention, the method and apparatus utilize two fiber optic bundles 13 and 15' shown in FIG. 5 and which share the same illumination fiber bundle 10 to form two detectors. The bundles 13 and 15' are spaced apart a distance less than the width of the smallest segment (which in this case is shown to be the air segment A) in order to detect the interface between an air segment A and any one of the liquid segments including the sample plus first reagent and second reagent S/R1/R2, the first wash W1, the second wash W2, the third reagent R3 or the magnetic particle suspension MP. The segments are sampled at a rate at least twice the flow rate.

The bundles 13 and 15' are both 0.36 mm in diameter and have a center to center spacing of 0.64 mm. The centers of the bundles are spaced 0.35 mm from the nearest edge of bundle 14.

The output from each of bundles 13 and 15' is fed to photodiodes 16 and 16', the outputs of which are received by comparators 17 and 17' and compared to reference voltages 18 and 18' and the outputs 19,19' are applied to logic circuit 20 which produces two output signals 21,22, one specifying the fact that an interface has occurred and the other specifying the direction that the interface is traveling in, i.e., left or right as shown in FIG. 4.

Figure 6:
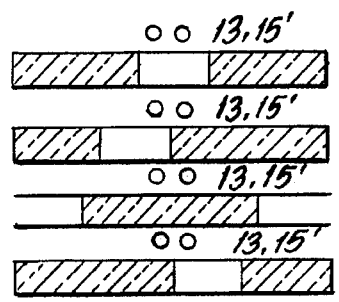
FIG. 6 is a logic state table for the embodiment of FIG. 4.

Logic circuit 20, is implemented by using conventional NAND, AND or NOR gates or similar logic embodied in software using a computer chip, based upon the unique set of logic states shown in FIG. 6 for the output on control signals 19, 19'.

It is understood that the embodiments described hereinabove are merely illustrative and are not intended to limit the scope of the invention. It is realized that various changes, alterations, rearrangements and modifications can be made by those skilled in the art without substantially departing from the spirit and scope of the present invention.

What is claimed is:

1. An apparatus for detecting a liquid/gas interface flowing in a transparent tube, comprising: means for directing light through a transparent tube orthogonal to a longitudinal axis thereof such that the directed light passing through the tube when filled with liquid thereat will extend substantially within a predetermined zone and when filled with gas thereat will extend beyond the predetermined zone comprising a first fiber optic bundle; a second fiber optic bundle disposed diametrically opposite to said first fiber optic bundle parallel thereto and positioned beyond said predetermined zone for receiving only light passing through the tube and extending beyond said predetermined zone; and means solely responsive to the amount of light received by the second fiber optic bundle for producing an output signal representative of a liquid/gas interface flowing in the tube.

2. The apparatus according to claim 1, wherein the means for producing the output signal comprises means for producing a binary signal which changes levels upon a change from liquid to gas and gas to liquid in the tube.

3. The apparatus according to claim 1, further comprising a third fiber optic bundle disposed diametrically opposite the first fiber optic bundle and positioned within the predetermined zone for receiving light for analysis of a component of the liquid.

4. The apparatus according to claim 3, wherein the first fiber optic bundle illuminates the second and third fiber optic bundles.

5. An apparatus for detecting a liquid/gas interface flowing in a transparent tube, comprising: means for directing light through a transparent tube orthogonal to a longitudinal axis thereof such that the directed light passing through the tube when filled with liquid thereat will extend substantially within a predetermined zone and when filled with gas thereat will extend beyond the predetermined zone comprising a first fiber optic bundle; a second fiber optic bundle disposed diametrically opposite to said first fiber optic bundle parallel thereto and positioned beyond said predetermined zone for receiving only light passing through the tube and extending beyond said predetermined zone; means responsive to the amount of light received by the second fiber optic bundle for producing an output signal representative of a liquid/gas interface flowing in the tube; and means for detecting the direction of flow in the transparent tube comprising a fourth fiber optic bundle positioned beyond the predetermined zone and adjacent the second fiber optic bundle and means receptive of the output signal from the fourth bundle for producing an output signal and means receptive of the output signals to produce control signals representative of a liquid/gas interface and the direction of flow of the interface in the tube.

6. The apparatus according to claim 5, wherein the means for producing the control signals comprises means for producing binary signals.

7. The apparatus according to claim 5, wherein the first fiber optic bundle illuminates the second and fourth fiber optic bundles.

8. An apparatus for detecting a liquid/gas interface flowing in a transparent tube, comprising: means for directing light through a transparent tube orthogonal to a longitudinal axis thereof such that the directed light passing through the tube when filled with liquid thereat will extend substantially within a predetermined zone and when filled with gas thereat will extend beyond the predetermined zone comprising a first fiber optic bundle, wherein the predetermined zone extends from 23 to 45 degrees off of a longitudinal axis of the first fiber optic bundle; a second fiber optic bundle disposed diametrically opposite to said first fiber optic bundle parallel thereto and positioned beyond said predetermined zone for receiving only light passing through the tube and extending beyond said predetermined zone; and means responsive to the amount of light received by the second fiber optic bundle for producing an output signal representative of a liquid/gas interface flowing in the tube.

9. A method for detecting a liquid/gas interface flowing in a transparent tube, comprising the steps of: directing light in a first fiber optic bundle through a transparent tube orthogonal to a longitudinal axis thereof such that the directed light passing through the tube when filled with liquid thereat will extend substantially within a predetermined zone and when filled with gas thereat will extend beyond the predetermined zone; receiving light with a second fiber optic bundle parallel to the first fiber optic bundle and at a position diametrically opposite to a position from which light is directed and beyond the predetermined zone to receive only light passing through the tube and extending beyond said predetermined zone; and producing an output signal representative of a liquid/gas interface flowing in the tube solely in response to the amount of light received by the second fiber optic bundle.

10. The method according to claim 9, wherein the step of producing the output signal comprises producing a binary signal which changes levels upon a change from liquid to gas and gas to liquid in the tube.

11. A method for detecting a liquid/gas interface flowing in a transparent tube, comprising the steps of: directing light in a first fiber optic bundle through a transparent tube orthogonal to a longitudinal axis thereof such that the directed light passing through the tube when filled with liquid thereat will extend substantially. within a predetermined zone and when filled with gas thereat will extend beyond the predetermined zone; receiving light with a second fiber optic bundle parallel to the first fiber optic bundle and at a position diametrically opposite to a position from which light is directed and beyond the predetermined zone to receive only light passing through the tube and extending beyond said predetermined zone; producing an output signal representative of a liquid gas interface flowing in the tube in response to the amount of light received; detecting the direction of flow in the transparent tube comprising the steps of positioning a fourth fiber optic bundle outside the predetermined zone and adjacent the second bundle; producing output signals from the fourth bundle representative of a liquid/gas interface flowing in the tube in response to the amount of light received; and comparing the output signals from the second and fourth bundles to produce control signals representative of a liquid/gas interface and the direction of flow of the interface from the output signals.

12. The method according to claim 11, further comprising the steps of positioning a third fiber optic bundle diametrically opposite the first fiber optic bundle within the predetermined zone for receiving light only for analysis of a component of the liquid.

13. The method according to claim 11, wherein the step of producing the control signals comprises producing binary signals.

* * * * *